(12) United States Patent
Reynard et al.

(10) Patent No.: US 11,896,452 B2
(45) Date of Patent: Feb. 13, 2024

(54) METHOD FOR VIRTUAL SETUP WITH MIXED DENTITION

(71) Applicants: Carestream Dental Technology Topco Limited, London (GB); Delphine Reynard, Montreuil (FR); Sabrina Capron-Richard, Croissy-Beaubourg (FR); Sebastien Henry, Croissy-Beaubourg (FR); Shoupu Chen, Rochester, NY (US); Aude Lagardere, Croissy-Beaubourg (FR); Jean-Pascal Jacob, Croissy-Beaubourg (FR)

(72) Inventors: Delphine Reynard, Montreuil (FR); Sabrina Capron-Richard, Croissy-Beaubourg (FR); Sebastien Henry, Croissy-Beaubourg (FR); Shoupu Chen, Rochester, NY (US); Aude Lagardere, Croissy-Beaubourg (FR); Jean-Pascal Jacob, Croissy-Beaubourg (FR)

(73) Assignee: CARESTREAM HEALTH, INC., Rochester, NY (US)

( * ) Notice: Subject to any disclaimer, the term of this patent is extended or adjusted under 35 U.S.C. 154(b) by 729 days.

(21) Appl. No.: 16/494,504

(22) PCT Filed: Mar. 14, 2018

(86) PCT No.: PCT/US2018/022287
§ 371 (c)(1),
(2) Date: Sep. 16, 2019

(87) PCT Pub. No.: WO2018/170030
PCT Pub. Date: Sep. 20, 2018

(65) Prior Publication Data
US 2020/0085548 A1    Mar. 19, 2020

Related U.S. Application Data

(60) Provisional application No. 62/472,123, filed on Mar. 16, 2017.

(51) Int. Cl.
*G06T 19/00* (2011.01)
*A61C 13/34* (2006.01)
(Continued)

(52) U.S. Cl.
CPC ............ *A61C 13/34* (2013.01); *A61B 6/032* (2013.01); *A61B 6/14* (2013.01); *A61B 6/145* (2013.01);
(Continued)

(58) Field of Classification Search
CPC ......... A61C 13/34; G06T 7/0012; G06T 7/62; G06T 19/00; G06T 2207/10081
(Continued)

(56) References Cited

U.S. PATENT DOCUMENTS

| 5,882,192 A | 3/1999 | Bergersen |
| 8,929,635 B2 | 1/2015 | Chen et al. |

(Continued)

FOREIGN PATENT DOCUMENTS

| WO | WO 2018/022054 A1 | 2/2018 |
| WO | WO 2018/038748 A1 | 3/2018 |
| WO | WO 2018/101923 A1 | 6/2018 |

OTHER PUBLICATIONS

H. Akhoondali et al., "Rapid Automatic Segmentation and Visualization of Teeth in CT-Scan Data," Journal of Applied Sciences, 9(11):2031-2044, (2009).
(Continued)

*Primary Examiner* — Gordon G Liu
(74) *Attorney, Agent, or Firm* — ALSTON & BIRD LLP

(57) ABSTRACT

A method for visualizing patient dentition acquires a contour image of patient dentition and segments the contour image
(Continued)

to identify one or more segmented teeth. At least one deciduous tooth among the one or more segmented teeth is identified. A virtual model of a target dentition arrangement of the patient dentition is generated, wherein the at least one deciduous tooth is replaced by a replacement permanent tooth.

20 Claims, 11 Drawing Sheets

(51) Int. Cl.
*G06T 7/62* (2017.01)
*G06T 7/149* (2017.01)
*A61B 6/03* (2006.01)
*A61B 6/14* (2006.01)
*A61B 6/00* (2006.01)
*A61C 9/00* (2006.01)
*G06T 7/00* (2017.01)
*G06T 1/20* (2006.01)
*G06T 19/20* (2011.01)

(52) U.S. Cl.
CPC .......... *A61B 6/4085* (2013.01); *A61C 9/0046* (2013.01); *G06T 1/20* (2013.01); *G06T 7/0012* (2013.01); *G06T 7/149* (2017.01); *G06T 7/62* (2017.01); *G06T 19/20* (2013.01); *G06T 2200/24* (2013.01); *G06T 2207/10081* (2013.01); *G06T 2207/30036* (2013.01); *G06T 2219/2021* (2013.01)

(58) Field of Classification Search
USPC .......................................................... 433/29
See application file for complete search history.

(56) References Cited

U.S. PATENT DOCUMENTS

| | | | |
|---|---|---|---|
| 2003/0224314 A1* | 12/2003 | Bergersen | ................ A61C 7/08 433/6 |
| 2011/0191075 A1* | 8/2011 | Hultgren | ................ G06G 7/60 703/2 |
| 2015/0342545 A1* | 12/2015 | Bergersen | .............. G16H 30/40 378/62 |
| 2017/0076443 A1 | 3/2017 | Ye et al. | |
| 2018/0146934 A1* | 5/2018 | Ripoche | ................ G06T 17/20 |
| 2021/0153976 A1 | 5/2021 | Chen et al. | |

OTHER PUBLICATIONS

Tiziano Baccetti et al., "Skeletal effects of early treatment of Class III malocclusion with maxillary expansion and face-mask therapy," American Journal of Orthodontics and Dentofacial Orthopedics, 113(3):333-343 (Mar. 1998).

G.J. King et al., "Orthodontists' Perceptions of the Impact of Phase 1 Treatment for Class II Malocclusion on Phase 2 Needs," Journal of Dental Research, 78(11): 1745-1753 (Nov. 1999).

WIPO Application No. PCT/US2018/022287, PCT International Preliminary Report on Patentability dated Sep. 26, 2019.

WIPO Application No. PCT/US2018/022287, PCT International Search Report and Written Opinion of the International Searching Authority dated Jun. 8, 2018.

* cited by examiner

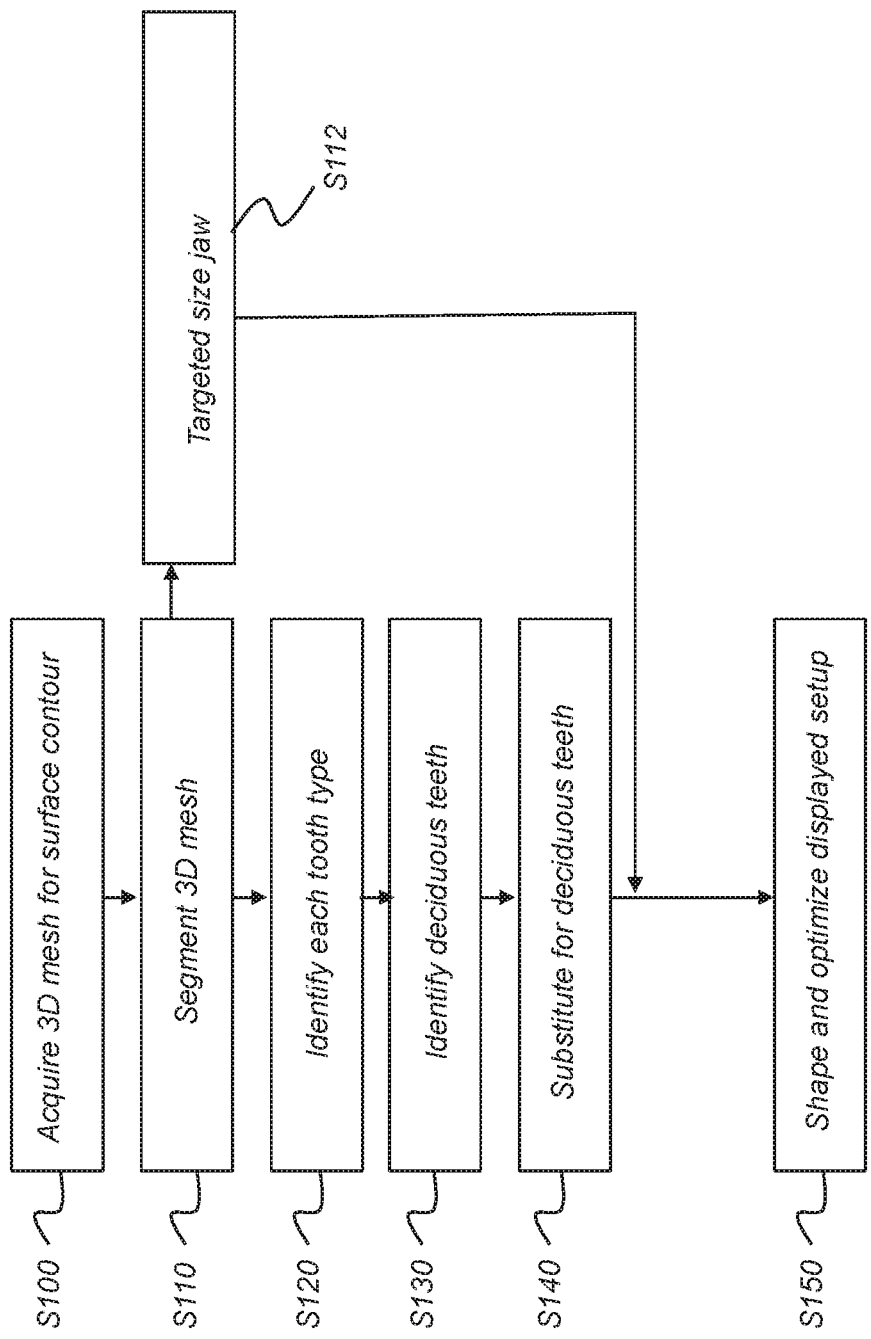

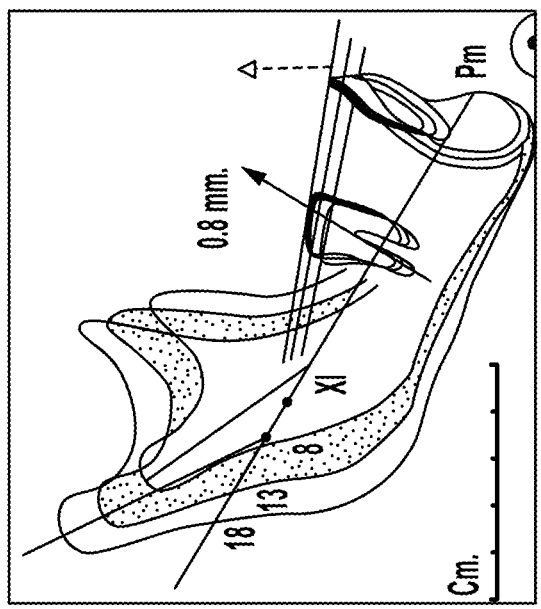
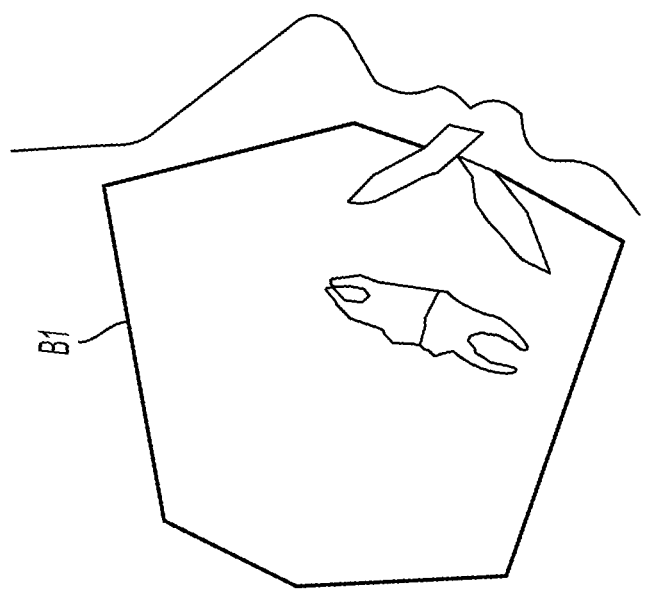
FIG. 5

METHOD FOR VIRTUAL SETUP WITH MIXED DENTITION

CROSS REFERENCE TO RELATED APPLICATIONS

This application claims the benefit of U.S. Provisional application Ser. No. 62/472,123, provisionally filed on Mar. 16, 2017, entitled "METHOD FOR DETERMINING A VIRTUAL SETUP IN MIXED DENTITION", in the names of Delphine Reynard and Shoupu Chen, incorporated herein in its entirety.

Commonly assigned related applications include:
U.S. Provisional Patent Application 62/550,013 entitled "Method of Optimization in Orthodontic Applications" to Chen et al.;
U.S. Pat. No. 8,929,635 entitled "Method and System for tooth Segmentation" to Chen et al.;
US Patent Application Publication No. 2017/0076443 entitled "Method and System for Hybrid Mesh Segmentation" to Wei et al.;
PCT Publication Number WO2018038748 entitled "Method and System for Hybrid Mesh Segmentation" to Chen et al.;
PCT Application Number PCT/US16/64102 entitled "Method and System for Braces Removal from Dentition Mesh" to Chen et al.; and
PCT Publication Number WO2018022054 entitled "Method and System for Dental Arch Mesh Model Manipulation" to Chen et al.

TECHNICAL FIELD

The present disclosure relates generally to orthodontics and more particularly to methods and/or apparatus for generating a virtual setup for a patient having mixed dentition.

BACKGROUND

Before orthodontic treatment for a treatment commences, it is current practice to create a virtual 3D model of an initial tooth arrangement of the patient's upper and lower jaw. The virtual teeth in this 3D model are then segmented and can be displaced relative to each other to form a "virtual setup" (e.g., target or final tooth arrangement), which can simulate an orthodontic treatment plan.

In orthodontics, practitioners use the virtual setup to help them plan the treatment sequence for each patient. The virtual setup that is generated helps to model/visualize treatment parameters like tooth size-arch length discrepancy and to determine whether or not extraction or surgery are required.

Numerous applications have been developed and are now available to generate a virtual setup of patient dentition. One of the aims of the virtual setup is to determine whether or not there is sufficient space in the maxilla and mandible jaw for all the teeth, and to visualize the effects of the treatment plan on the occlusion.

More than one technique can be used to acquire a 3D model of teeth. In one approach, the patient's mouth can be scanned using an intra oral camera that uses triangulation, for example, acquiring multiple image frames before reconstructing the 3D surface model of the teeth. Alternatively, positive physical casts representing the patient's lower and upper jaw can also be scanned by the intra oral camera to generate the 3D surface model of the teeth.

Furthermore, the two positive physical casts representative of the mandible and the maxillary of the patient can be scanned using a cone beam computed tomography (CBCT) x-ray device to generate 3D volume model of the teeth. A CBCT device can include a gantry supporting an X-ray source and a sensor opposite the source, with the gantry rotating about a support that holds the plaster cast. A number of 2D frames is acquired by the sensor during this rotation. A 3D matrix of grey levels can be reconstructed using standard algorithms.

The terms "permanent teeth" and "adult teeth" have their conventional meaning as used in the dental arts and are considered synonymous, both referring to the teeth that replace the deciduous or "primary" teeth as the patient matures.

It remains difficult to achieve accurate virtual setup for growing patient (e.g., with mixed dentition including a combination of deciduous and permanent teeth). Therefore, there is a need to improve the accuracy of virtual setup for younger orthodontic patients.

SUMMARY

It is an object of the present disclosure to advance the art of orthodontic planning and treatment.

In one aspect, exemplary method and/or apparatus embodiments according to the disclosure relate to determining a virtual setup in a mixed dentition. In one exemplary embodiment, the deciduous teeth are detected and replaced in the virtual setup with a substituting tooth. In another exemplary embodiment, the jaw growth is also taken into account.

Certain exemplary method and/or apparatus embodiments according to the application are directed to determining a virtual setup in a mixed dentition. One exemplary method embodiment can include, individually or in combination:
a) providing a segmented 3D mesh of the patient teeth, each segmented tooth comprising a mesh and a teeth margin;
b) labeling the segmented teeth;
c) identifying, among the segmented teeth, at least one deciduous tooth having a first size and a first shape; and/or
d) generating a virtual setup, substituting a replacement tooth for the at least one identified deciduous tooth, wherein the replacement tooth has a second size and a second shape and wherein the second size and second shape of the corresponding replacement tooth is different from the first size and first shape of the deciduous tooth by a feature-to-feature dimensional difference of more than +/−10%.

Exemplary method and/or apparatus embodiments address one problem by substituting the deciduous tooth with a corresponding replacement tooth in the virtual setup, such that the replacement tooth may have size and shape that are similar to the size, shape, and fit of the future permanent teeth. As used herein, the term "similar" or "similarity" requires that the two teeth fit at the proper tooth position within the jaw.

In one exemplary embodiment, two teeth are similar if their size and surface feature dimensions are within 10%. In another exemplary embodiment, two teeth are similar if their shape and size are within 5% or preferably 3%. In practice, shape similarity can be quantified by calculating the Dice coefficient, also variously termed the Sorensen-Dice coefficient or Sorensen-Dice Index, which can be applied to shapes using techniques well known to those skilled in the volume image segmentation arts. Chain codes, familiar to those skilled in the imaging arts, can alternately be used as a shape metric.

In an exemplary embodiment, a segmented CBCT 3D volume can be provided or acquired. In another exemplary embodiment, the corresponding substituting tooth is an unerupted permanent tooth from the segmented CBCT 3D volume.

Certain exemplary method and/or apparatus embodiments of the present disclosure are directed to systems for providing a virtual setup in a mixed dentition and/or methods for using the same. Exemplary system embodiments can include, individually or in combination:

- An input component that receives a segmented 3D mesh of the patient teeth, each segmented tooth comprising a mesh and a teeth margin,
- A labeling component that labels the segmented teeth,
- A deciduous tooth determination component that determines a first size of the deciduous tooth, and
- A virtual setup component that provides a virtual setup by substituting the deciduous tooth with a corresponding substituting tooth, the substituting tooth having a second size and a second shape and wherein the second size and second shape of the corresponding substituting tooth is different from the first size and first shape of the deciduous tooth.

One exemplary system embodiment also includes a display component for displaying the provided virtual setup. Exemplary embodiments herein are also related to providing a virtual setup. One exemplary method embodiment can include, individually or in combination:

a) Providing a segmented 3D mesh of the patient teeth, each segmented tooth comprising a mesh and a teeth margin;
b) Providing user preferences;
c) Determining a set of simulation options based on the user preferences;
d) Providing a virtual setup based on the set of simulation options;
e) Determining a set of metrics corresponding to the provided virtual setup; and/or
f) Displaying the virtual setup.

One exemplary system embodiment can include, individually or in combination:

a. An input component that receives a mesh model of the segmented patient teeth, each segmented tooth comprising a mesh and a tooth margin;
b. A user preferences component that provides the user preferences;
c. A simulation options component that determines a set of simulation options based on the user preferences;
d. A virtual setup component for providing the virtual setup based on the set of simulation options;
e. A metrics component that determines a set of metrics corresponding to the provided virtual setup; and/or
f. A display for displaying at least the virtual setup.

According to one aspect of the disclosure, there is provided a method that can include:

receiving a plurality of segmented teeth from an virtual model of an initial tooth arrangement;
identifying at least one deciduous tooth among the plurality of segmented teeth; and
generating a virtual setup of a target tooth arrangement where the at least one deciduous tooth is replaced by a corresponding permanent tooth model.

These objects are given only by way of illustrative example, and such objects may be exemplary of one or more embodiments of the invention. Other desirable objectives and advantages inherently achieved in the present disclosure may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 4 is a logic flow diagram showing use of jaw size data within virtual setup.

FIG. 5 shows an example of a Bjork-Jarabak polygon.

DESCRIPTION OF EMBODIMENTS

Figure 1:
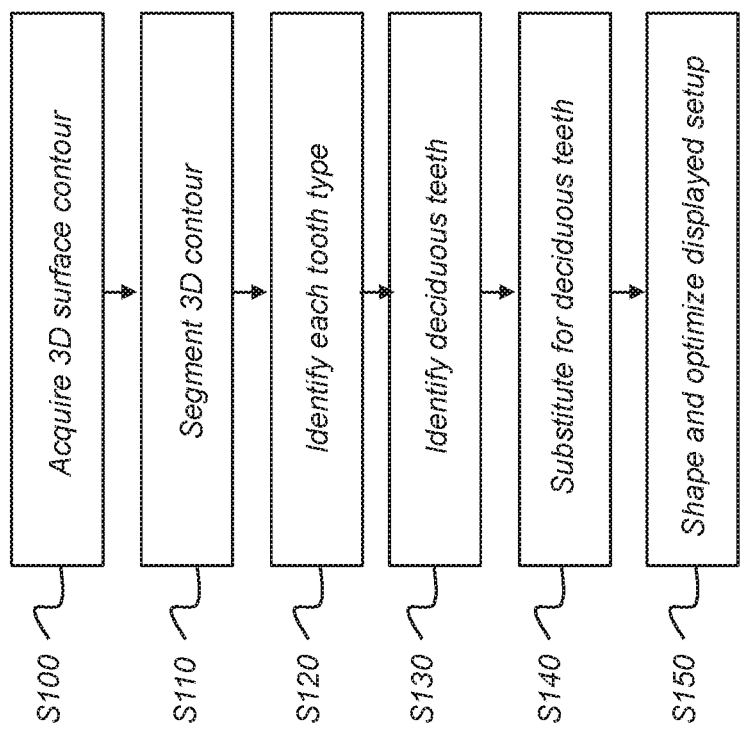
FIG. 1 is a logic flow diagram that shows a sequence for improved orthodontic planning for patients with deciduous teeth.

The following is a description of embodiments, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

The term "exemplary" indicates that the description is used as an example, rather than implying that it is an ideal.

The term "in signal communication" as used in the application means that two or more devices and/or components are capable of communicating with each other via signals that travel over some type of signal path. Signal communication may be wired or wireless. The signals may be communication, power, data, or energy signals which may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional or volume images and a pixel for 2-dimensional (2-D) images. For the purposes of the description herein, the terms voxel and pixel can generally be considered equivalent, describing an image elemental datum that is capable of having a range of numerical values. Voxels and pixels have attributes of both spatial location and image data code value.

"Patterned light" is used to indicate light that has a predetermined spatial pattern, such that the light has one or more features such as one or more discernable parallel lines, curves, a grid or checkerboard pattern, or other features having areas of light separated by areas without illumination. In the context of the present disclosure, the phrases "patterned light" and "structured light" are considered to be equivalent, both used to identify the light that is projected toward a subject in order to derive contour image data.

In the context of the present disclosure, the terms "viewer", "operator", and "user" are considered to be equivalent and refer to the viewing practitioner, technician, or other person who can operate an imaging system, camera, or scanner and may also view and manipulate the presentation of an image, such as a dental image, on a display monitor.

A "viewer instruction", "practitioner instruction", "operator instruction", or "operator command" can be obtained from explicit commands entered by the viewer such as by clicking a button on the camera or scanner or by using a computer mouse or by touch screen or keyboard entry. With respect to entries entered on an operator interface, such as an interface using a display monitor and keyboard, for example, the terms "command" and "instruction" may be used interchangeably to refer to an operator entry.

In the context of the present disclosure, the term "imaging apparatus" relates to a device that is enabled to acquire any of a number of types of images, using an appropriate source of light energy or radiation, including various types of reflectance imaging, structured light imaging, panoramic imaging, x-ray imaging, computed tomography (CT) imaging, cone beam computed tomography (CBCT) imaging, or other imaging type.

The terms "3-D model", "point cloud", "3-D surface", "virtual model", "surface contour model", and "mesh" may be used synonymously in the context of the present disclosure describing an image that characterizes surface contour, structure, and features, without providing data from within the volume within the surface. The dense point cloud is formed using techniques familiar to those skilled in the volume imaging arts for forming a point cloud and relates generally to methods that identify, from the point cloud, vertex points corresponding to surface features. The dense point cloud is thus generated using the reconstructed contour data from one or more reflectance images or from other volume image data. Dense point cloud information serves as the basis for a polygon model at high density for the teeth and gum surface.

The terms "permanent teeth" and "adult teeth" have their conventional meaning as used in the dental arts and are considered synonymous, both referring to the teeth that replace the deciduous or "primary" teeth as the patient matures.

Recent studies have expressed interest in early orthodontics treatment, addressing the needs of younger patients who show signs of developing orthodontic problems. According to some authors, for example, early treatment of Class II malocclusion reduces the severity of the discrepancy and also the difficulty and length of treatment with fixed appliances [King, 1999]. Similarly, it is also advisable to detect Class III malocclusions of a patient at an early age, while still having deciduous or early mixed dentition. In his study, Baccetti shows that the earlier the treatment is carried out, the greater the chance of success, which results from skeletal changes rather than dental compensation.

Dr. Allan Brodie at the University of Illinois published an article with two important conclusions: first that a definite correlation exists between success in treatment and good facial growth, and second that actual bone changes accompanying orthodontic treatment seem to be restricted to the alveolar bone.

Several analyses exist to evaluate the amount of space needed for succeeding permanent teeth within the arch. Some of the studies use the correlation between the sizes of the mandibular incisors and the combined sizes of cuspids and bi-cuspids in either arch to evaluate the space needed (Moyer's Mixed Dentition analyses, or Tanaka and Johnson Analysis). Another analysis such as leeway analysis makes a link between the sizes of the deciduous vs. permanent teeth.

It remains difficult to achieve accurate virtual setup for growing patient (e.g., with mixed dentition including a combination of deciduous and permanent teeth); for example, the eventual size of permanent teeth and the actual size of the adult jaw for a growing patient can be difficult to predict.

Exemplary embodiments of the present disclosure address problems for orthodontic analysis and/or planning (e.g., described herein) by providing selectable combinations of tools for visualization of patient dentition corrected to compensate for deciduous teeth.

FIG. 1 is a logic flow diagram showing an overall sequence for improved orthodontic planning for patients with deciduous teeth. This sequence generates a virtual model of the dentition, termed a dental "setup" or "virtual setup" (e.g., target or final tooth arrangement) in the context of the present disclosure and displayed to the practitioner. Exemplary virtual dental setup embodiments show a combination of existing teeth along with replacement model teeth that serve as substitutes for deciduous teeth. Various components/processes then are able to modify the virtual dental setup based on processing instructions and various parameters that can be set by the practitioner.

The 3D visualization that is provided by the virtual setup allows the practitioner to simulate actions including manipulation, replacement, and repositioning of teeth (e.g., orthodontic treatment) and to view simulated results of these actions as 3D volume images, presented as a virtual setup. It must be emphasized that subsequent description for activities such as "tooth removal", "substitution", "replacement" and similar functions correspond to procedures that can eventually be carried out on the patient's teeth, but more particularly within the virtual setup, relate to "virtual" operations performed upon the corresponding data generated for the virtual presentation. In the virtual setup, these processing activities can be fully automated or may allow varying amounts of interactive operation (e.g., semi-automatic or manual) for executing operator instructions.

In an acquisition step S100, a 3-D surface mesh or other suitable surface contour model is obtained, providing an initial model (e.g., initial upper/lower tooth arrangement) that characterizes the surface of teeth, supporting tissue, and other features within the dental arch. The initial 3-D surface mesh or other contour representation provides a framework for generating the dental arch setup used for developing and visualizing orthodontic treatment, for example. The 3-D surface mesh or other contour can be acquired using a surface contour imaging apparatus that uses patterned or structured light or using a computed tomography apparatus such as a CBCT imaging system that generates 3-D volume data for the patient. A segmentation step S110 applies image segmentation logic to define individual teeth from within the acquired 3-D mesh or other surface contour model. An identification step S120 identifies the tooth type or "labels" the tooth type for each segmented tooth.

Continuing with the FIG. 1 sequence, a deciduous tooth identification step S130 then identifies deciduous teeth among the segmented tooth structures. A substitution step S140 performs the procedure to remove each identified deciduous tooth from the arch and replace it with a corresponding adult or permanent tooth model having a different size and differing in shape from the deciduous tooth. An optimization step S150 performs the arch shaping and optimization for improved patient occlusion according to the tooth substitution; and then, the virtual setup that is used to plan patient treatment can be displayed, stored, or transmitted.

Acquiring a 3D Mesh or Point Cloud of the Patient Teeth in Acquisition Step S100

The 3D model of patient dentition can be acquired using an intraoral scanner that scans the mouth of the patient directly or using a multi-view radiographic imaging mode, such as a panoramic radiographic apparatus that acquires and assembles multiple views of patient dentition, each view captured at a different angle with respect to the patient's head. The 3D model can alternately be acquired using a CBCT scan of an impression obtained from the patient using conventional practices and materials. Alternatively, the CBCT x-ray device can scan the patient to generate a 3D volume model of the teeth.

Figure 2:
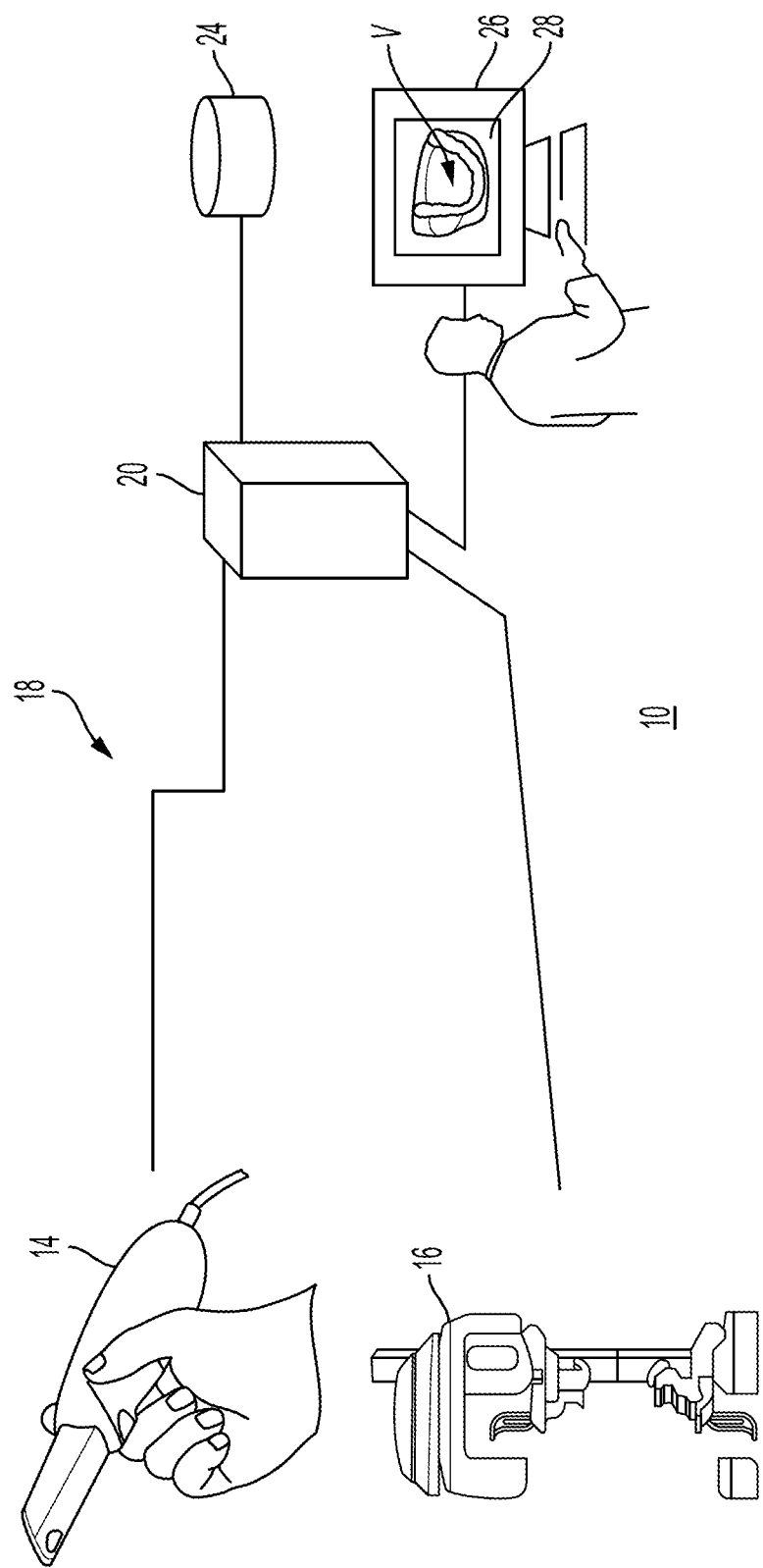
FIG. 2 is a schematic diagram that shows components of a dental imaging system for obtaining and displaying mesh and point cloud image content for surfaces of patient dentition.

FIG. 2 is a schematic diagram that shows components of a dental imaging system 10 for obtaining and displaying patient images of various types, including mesh or point cloud images or other surface contour models of patient dentition during different stages of a treatment session. Dental imaging system 10 includes at least one imaging apparatus 18 for 3D surface image acquisition, which may be a digital camera 14 such as an intra-oral camera or scanner, such as a structured light imaging scanner using reflectance imaging, or an extraoral dental imaging apparatus such as a dental cone-beam computed tomography (CBCT) system 16 for generating volume images of tooth surface and related structure. Other types of imaging apparatus 18 could also be employed for obtaining images of teeth and supporting structures, gums, and related tissue, such as panoramic imaging apparatus, or ultrasound imaging apparatus. In addition, various types of diagnostic measurement instrumentation may also be provided for working with dental imaging system 10, as described in more detail subsequently.

Still referring to FIG. 2, a host processor 20, a computer or other type of dedicated control logic processor for obtaining, processing, and storing image data from the imaging apparatus 18, is also part of dental imaging system 10, along with one or more displays 26 for viewing image results. Each display 26 can have a graphical user interface (GUI) 28 for entry of viewer instructions. GUI 28 can use a touch screen or other instruction entry device, such as a mouse or other pointer. According to an embodiment of the present disclosure, display 26 and associated GUI 28 provide the display and interactive functions of a virtual setup V that is used by the dental practitioner and is described in detail subsequently.

Host processor 20 is in data communication with, and provides image processing for, camera 18 and other volume image capture devices that can acquire the 3-D mesh or point cloud or other types of surface contour models/data and provide at least a portion of the processing needed for providing virtual setup V. In addition, host processor 20 can also be in networked data communication with a database of patient records, stored internally or on a networked host or server, for example. A computer-accessible memory 24 is also provided, which may be a non-volatile memory storage device used for longer term storage, such as a device using magnetic, optical, or other data storage media. In addition, computer-accessible memory 24 can comprise a volatile electronic memory such as a random access memory (RAM), within or otherwise in data communication with host processor 20, that is used for shorter term data storage, such as memory used in conjunction with a display device for temporarily storing image content as a display buffer, or memory that is employed to store a computer program having instructions for controlling one or more computers to practice the processing method according to an embodiment of the present disclosure.

Providing a Segmented 3D Mesh of the Patient Teeth in Step S110

Once acquired, the 3D point cloud, mesh model, or other surface contour model is segmented. Segmentation of teeth represented using a mesh or other model allows the practitioner to identify and isolate the crown and other visible portions of the tooth from gums and related supporting structure. In FIG. 1 segmentation step S110, the 3D mesh is processed in order to define the contour boundaries of the individual teeth. In some embodiments, segmented teeth can include crowns and roots.

Segmentation processing can be fully automated or can be manually assisted in some way, such as by the entry of seed data or other initialization data according to operator entered instructions. There are a number of segmentation methods familiar to those skilled in the volume imaging arts and described in the literature for tooth segmentation. Methods that can be used for tooth segmentation can include snake-based segmentation, iterative segmentation techniques, and region growing, for example, as well as other techniques well known to those skilled in the image processing arts. Preferable exemplary segmentation methods can be found in commonly assigned US Patent Application Publication No. 2017/0076443 entitled "Method and System for Hybrid Mesh Segmentation" to Wei et al., incorporated herein in its entirety.

The virtual 3-D model can be processed automatically, manually or semi-automatically to define the contour and margins of the teeth (generally termed tooth margin), and to obtain a virtual model such as a mesh for each tooth (termed a tooth mesh). Using the 3-D mesh or other surface contour model, a significant number of features can be identified for each tooth, including axis (Mesio-distal, vestibule-lingual, main axis), cusps, fossae, and largest contour, for example.

Other reference for tooth segmentation is hereby made to the following:

Akhoondali et al. in "Rapid Automatic Segmentation and Visualization of Teeth in CT-Scan Data", *Journal of Applied Sciences*, pp 2031-2044, (2009); and Gao et al. in "Tooth Region Separation for Dental CT Images", *Proceedings of the* 2008 *Third International Conference on Convergence and Hybrid Information Technology*, pp 897-901, (2008).

Reference is further hereby made to:

King G J, Wheeler T T, McGorray S P, Aiosa L S, Bloom R M, Taylor M G. "Orthodontists' perceptions of the impact of phase 1 treatment for Class II malocclusion on phase 2 needs". *J Dent Res*. 1999 November; 78(11):1745-53; and Baccetti T, McGill J S, Franchi L, McNamara J A Jr, Tollaro I. "Skeletal effects of early treatment of Class III malocclusion with maxillary expansion and face-mask therapy". *Am J Orthod Dentofacial Orthop*. 1998 March; 113(3): 333-43.

Previous attempts for tooth segmentation in CBCT volumes can be distinguished in either of two classes, based upon whether or not these approaches use energy-based formulation.

In the latter case, not employing energy-based criteria, are watershed-based methods (Sepehrian et al. 2013), manually seeded region-growing (Zhang 2011) or mean-shift clustering (Mortaheb et al. 2013). While such methods are usually fast, their results lack in precision because these methods don't take into account the dental context and factors such as metal artifacts and bone intensity similarity, for example.

Most state-of-the-art segmentation efforts use some sort of energy-based criteria. Examples of energy-based segmentation approaches include level-set framework (Gao et al. 2010, Hosntalab et al. 2008) or graph-cut formulation (Hiew et al. 2010) to minimize an energy problem. Such approaches allow inclusion of context-specific information (gradient, shape, texture, etc.) leading to accurate results within a reasonable computation time. For most of the methods, some user input is needed to indicate specific points inside the tooth (such as the center of the crown or the apex). Once the tooth is segmented inside the volume, the method uses a surface evolution algorithm using a marching cube to obtain a mesh of the tooth. Commonly assigned U.S. Pat. No. 8,929,635 to Chen et al., cited previously, provides another exemplary method for segmentation of an unerupted tooth in the CBCT volume.

Tooth Identification or Labeling in Steps S120 and S130

The number (label) of each tooth can also be determined (e.g., automatically, semi-automatically, and/or manually) using any of a number of dental tooth numbering systems, including well-established standard systems. Once this label is assigned to a deciduous tooth, a significant amount of useful information is available for subsequent processing.

There are a number of standard tooth numbering systems. One widely used numbering system that is a standard for labeling teeth is the Palmer notation method, also known as the Zsigmondy or Grid system. Quadrant-based, the Palmer method counts outward from the center teeth in each quadrant of the mouth. For permanent teeth, numbering designation within each quadrant is in the range 1 through 8, with accompanying symbols that indicate the quadrant position.

Alternately, the Universal Numbering System, also known as the American system, assigns numeric labels as its designations, with the number 1 assigned as label to the upper molar at the right side of the patient and successive numbering advancing along the upper teeth, to the third molar on the upper left side, assigned number 16. The molar beneath number 16 is labeled number 17, with numbering continued to 32 as the last lower molar on the right side below number 1. Deciduous teeth are labeled using capital letters A-T. Letter A designates the upper first tooth on the right side. Letter T is assigned as label to the last tooth on the lower right side.

The ISO system, also known as ISO 3950, uses a 2-digit label for each tooth. The first digit is a quadrant reference; the second digit labels the tooth within the quadrant. Individual teeth are labeled from 1-8 starting from the center teeth. Quadrant numbering is from 1 to 4 for permanent teeth; numbers 5 to 8 are used to label primary teeth, wherein the upper right is 1, upper left 2, lower left 3, and lower right 4. A similar pattern applies for deciduous teeth using the ISO labeling system.

A deciduous tooth can be identified by a number of characteristics that distinguish deciduous from permanent teeth; most of these characteristics can allow ready classification from surface features. Distinguishing characteristics for deciduous vs. permanent teeth include size, overall morphology, enamel thickness, root arrangement, and crown height, for example. Such distinguishing characteristics can be automatically detected and measured in order to determine whether or not a tooth is most likely to be deciduous or permanent. Subsequent processing can use automatic methods for detection of deciduous teeth, semi-automatic detection methods or use manual designation methods, or both automatic and manual methods.

Substituting for Deciduous Teeth in Step S140

The model substitute tooth can be obtained from patient data. According to an embodiment of the present disclosure, a CBCT 3D volume acquisition can be performed to detect unerupted teeth of the patient that can be used as substitutes for deciduous dentition. A specific segmentation can be implemented for positive identification and spatial characterization of the unerupted corresponding teeth. Once the unerupted tooth is segmented, the practitioner can access shape and size information for the unerupted tooth, which can be used to identify a substitute model tooth for the deciduous tooth in the virtual setup.

Figure 3B:
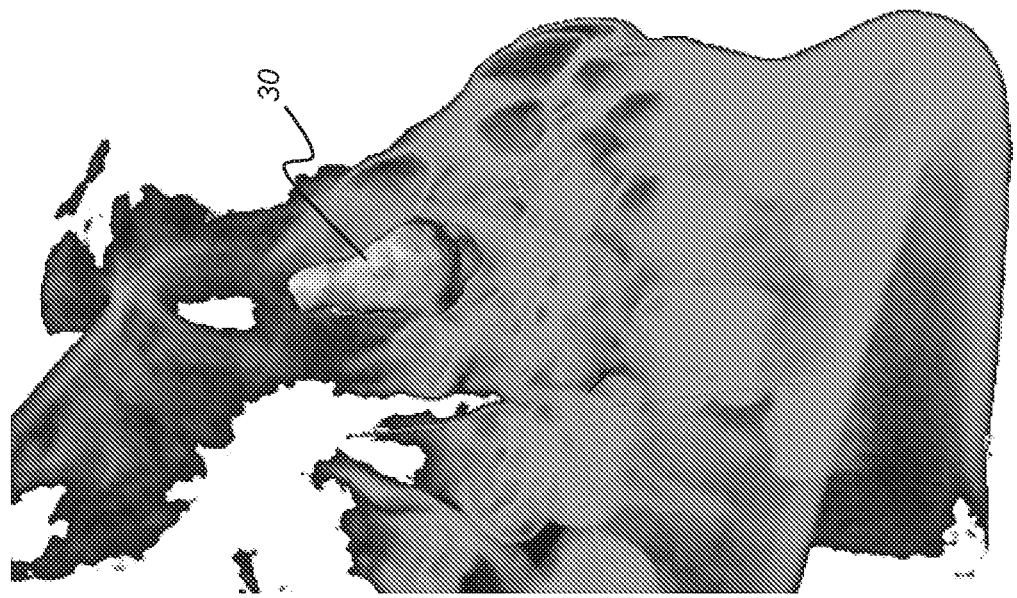
FIGS. 3A and 3B show imaging of an erupted tooth from panoramic image content.
Figure 3A:
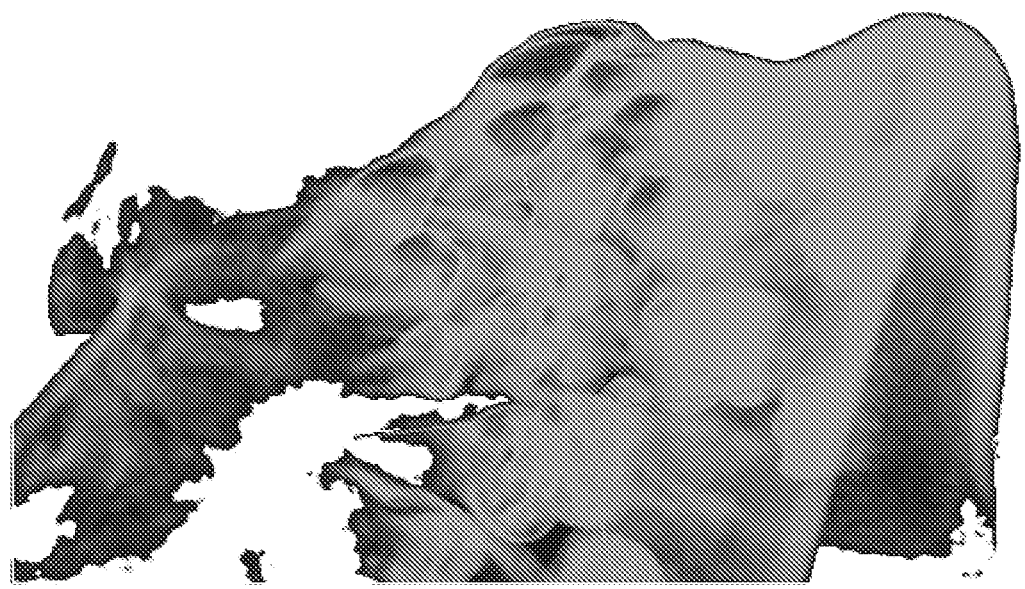

Alternatively, an unerupted tooth can also be detected using a panoramic radiography apparatus, as in the example images shown in FIGS. 3A and 3B. A specific segmentation can then be performed on the panoramic radiography and the associated size of an unerupted tooth 30 can be evaluated. The corresponding permanent tooth is then determined from a model tooth library based on the tooth label and the associated size. This corresponding tooth model is finally used as substitute, replacing the deciduous tooth in the virtual setup that is generated.

In 3D volume or panoramic radiography, erupted teeth as well as non-erupted teeth can be segmented. Each tooth on the 3D meshes can be associated to one of the teeth in the 3D Data. With this comparison, it is possible to calibrate and adjust scaling factors between the different acquisition methods (e.g., 3D mesh+3D volume or 3D mesh+panoramic).

In another alternative embodiment, predictive model analysis, well known to those skilled in the imaging arts, is used. Moyer's Mixed Dentition analysis can be used to predict the size of the permanent or adult teeth for a patient by measuring the size of the anterior teeth. Leeway analysis can also be used to predict the size of the permanent teeth based on the size of the corresponding deciduous teeth. The corresponding model tooth from this analysis can then be determined from a tooth library based on the tooth label and the associated size. This corresponding model tooth is finally used as substitute for the deciduous tooth in the virtual setup.

The substituting tooth for a deciduous tooth will have a size and shape appropriate for the permanent tooth that replaces the deciduous tooth.

In another alternative embodiment, the corresponding substituting tooth is determined from a tooth library based on the tooth label and an average size.

According to yet another alternative embodiment, the corresponding substituting tooth determination step is based on the symmetrical permanent tooth.

Determining the Jaw Size

One aspect of the tooth substitution in step S140 also relates to the size of the patient's jaw. The logic flow diagram of FIG. 4 shows an example sequence that uses jaw size data for the virtual setup that is generated. A jaw size determination step S112 determines the appropriate jaw size for the patient from the segmented 3D mesh data in segmentation step S110 and provides this data as additional input to optimization step S150.

In the art, several models exist for predicting the targeted jaw size. For example, the user may apply any one of the following:

Ricketts growth-forecasting methods;
The Johnston grid analysis; or
Bjork-Jarabak's Polygon, familiar to those skilled in the cephalometric arts, very useful to predict growth patterns both from qualitative and quantitative points of view (rotational pattern of jaw growth).

According to an embodiment of the present disclosure, the Bjork-Jarabak Polygon B1 is used for jaw size computation, as shown in the example of FIG. 5.

Generally, cephalometric radiography is performed to determine the jaw growth based on a predicting model and on cephalometric tracings.

If a 3D CBCT volume is available, the input parameters required for predicting the targeting jaw size may be evaluated on the 3D CBCT volume.

Virtual Setup, Shaping and Optimization Step S150

Referring back to the sequence of FIG. 1, optimization step S150 allows the imaging system 10 processor, with or without input from the operator, to form and to optimize a virtual setup for visualization of patient dentition. In one example embodiment, once the size of the targeted jaw is identified, the system displays the dentition for that jaw and manipulates tooth position to align the teeth appropriately where the deciduous teeth have been replaced by the permanent teeth on the targeted jaw.

Optionally, the user can also align teeth manually, either by-passing automatic alignment provided by processing logic, or manually adjusting or fine-tuning an automatic alignment provided by the system.

Automatic Virtual Setup

According to some exemplary method and/or apparatus embodiments of the present disclosure, an automatic virtual setup is dynamically provided to the orthodontist. The virtual setup that is provided is intended to correspond to established best practices. While it has special advantages for supporting orthodontic treatment of younger patients who still have some deciduous teeth, these embodiments can be applied for providing a virtual setup in many configurations and not limited to cases of mixed dentition.

Automatic virtual setup allows the orthodontist to visualize, in a very short time, the result of the treatment intended to be used and to make timely treatment adjustment if desired or required.

Figure 6:
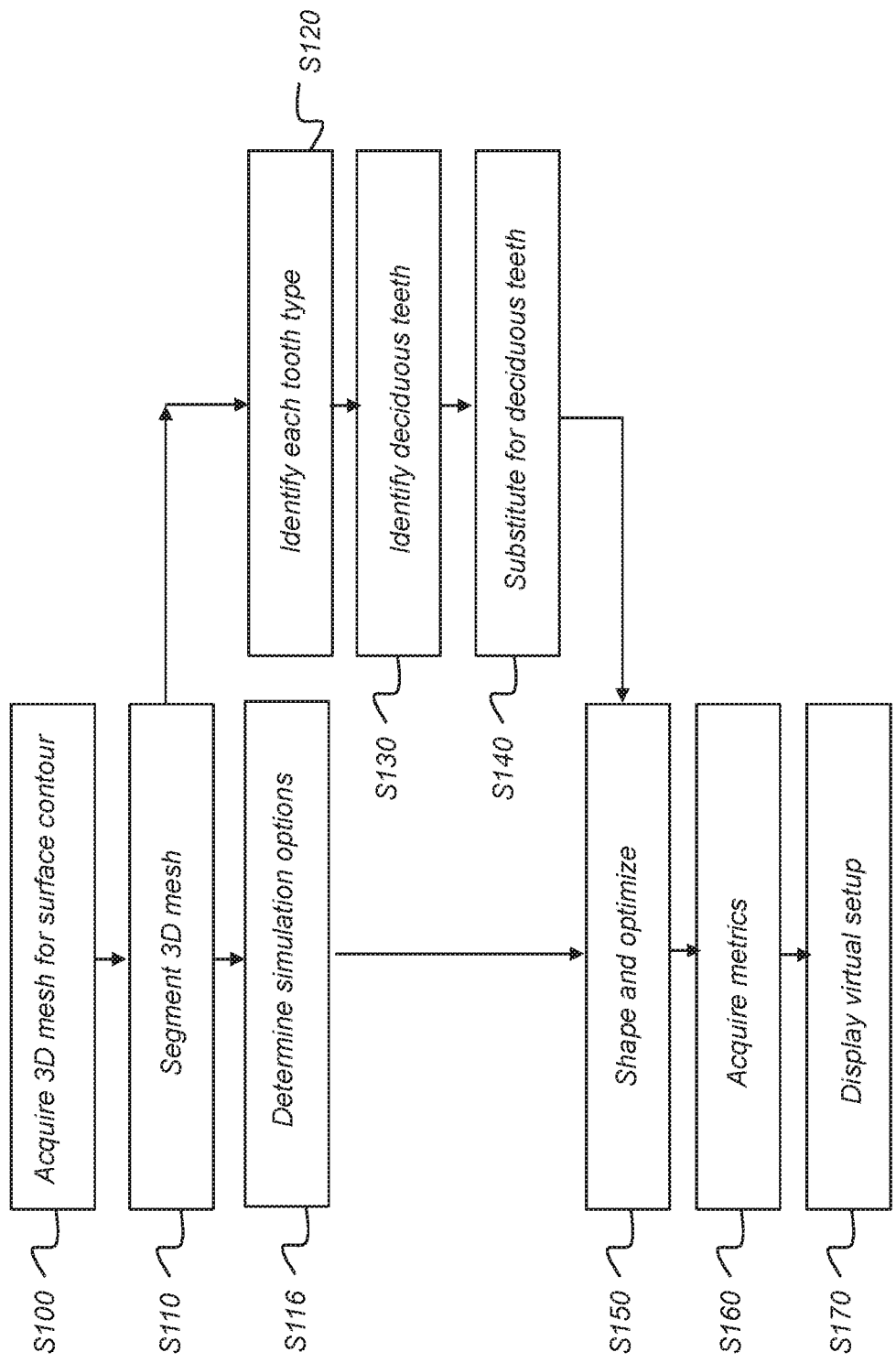
FIG. 6 is a logic flow diagram showing a sequence for optimization of patient dentition using simulation options.

An embodiment of the present disclosure also relates to a method for providing a virtual setup V, (e.g., see FIG. 2). As shown in the logic flow diagram of FIG. 6, the method can comprise:

a) acquiring a segmented 3D mesh of the patient teeth (e.g., in acquisition step S100 and a segmentation step S110);

b) providing one or more user preferences, such as those described in more detail subsequently (e.g., see FIG. 7, step S180);

c) identifying a set of simulation options based on the user preferences in a simulation options determination step S116;

d) generating a virtual setup V based on the identified set of simulation options in optimization step S150;

e) determining a set of metrics corresponding to the provided virtual setup in a metrics acquisition step S160; and f) displaying the generated virtual setup V and, optionally, the set of simulation options and set of metrics in a display step S170.

According to one embodiment, in order to reduce the time required for obtaining the virtual setup, the user preferences are provided at the beginning of the virtual setup planning process. These preferences are taken into account in subsequent operations/calculations performed (e.g., automated) by method steps/component elements/system logic. Alternative embodiments allow the user preferences to be provided at the end, during, or iteratively reviewed within the virtual setup planning process.

Figure 7:
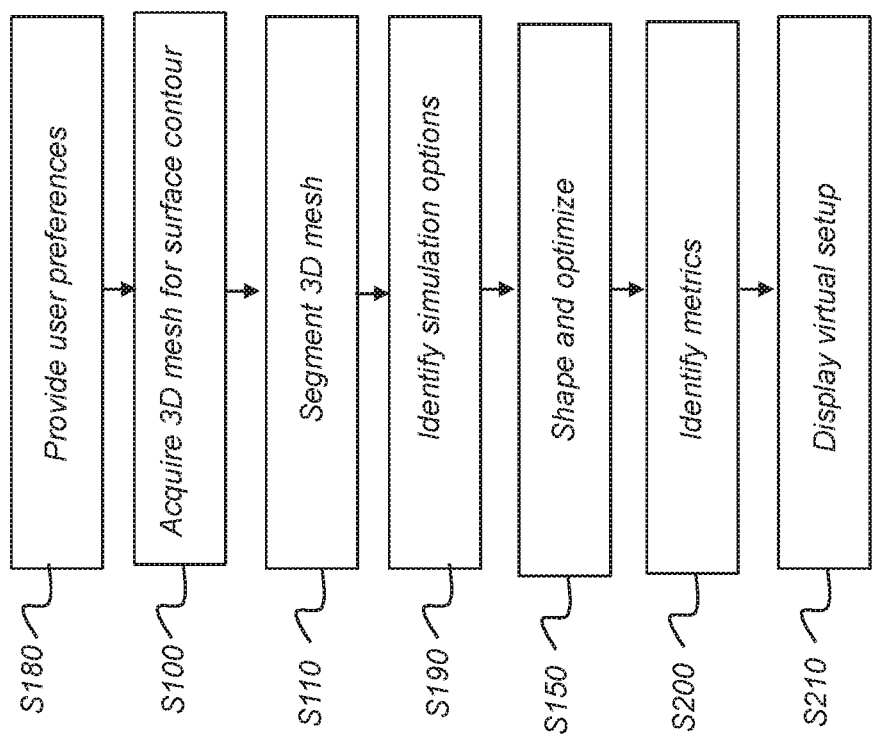
FIG. 7 is a logic flow diagram that shows a sequence for segmentation and display using optional user preferences and simulation options, with metrics.

The logic flow diagram of FIG. 7 shows an exemplary sequence for user preferences, simulation options, and metrics use and display. In a user preferences step S180, the operator can be presented with a listing of selectable user preferences. Preferences can determine how selected simulation functions operate.

User Preferences

User preferences are related to user daily practice and to the treatment compromises the user can accept. For instance and without limitation, the user preferences (e.g., step S180) may include one or more of the following, or a combination thereof:

Preferred type of arch, mandibular or maxillary;
Accept/reject inter-canine width expansion;
Flattening parameters for shaping the curve of Spee (related to curvature of the mandibular occlusal plane);
Arch expansion vs. tooth extraction;
In the case of tooth extraction, an ordering that indicates which tooth to extract first;
Tooth extraction vs. interproximal reduction;
Occlusal adjustment; and/or
Acceptance/rejection of treatment ending in molar class II.

As shown in FIG. 7, a segmented 3D mesh or equivalent surface contour is then provided using steps S100 and S110, described previously. A simulation options step S190 can then be executed, listing simulation options, as described subsequently. An optimization step S150 then provides the display of virtual setup V. A metrics identification step S200 follows, providing selectable metrics, as described in more detail subsequently. A display step S210 then displays the generated virtual setup and, optionally, the set of simulation options and set of metrics. In some example embodiments as shown in the logic flow diagram of FIG. 8, a simulation options adjustment step S208 allows operator adjustment of simulation options, as described subsequently.

For each user preference selected, one or more corresponding metrics threshold values can be defined. The defined threshold values can be used when determining the set of simulation options.

Once, the user preferences are provided to the system, a set of simulation options is determined. Simulation options selection determines what functions are performed on the arch where tooth substitution and arch shaping may be required.

The user preferences may also comprise a ranking in the proposed set or sequence of simulation operations, due to their relative impact on the jaw. Indeed, when multiple sets of simulation options are available, the method can initially select the set of simulation options inducing the least modification to the existing jaw. If a jaw growth model is used, the method can select the set of simulation options introducing the least modification to predicted jaw growth.

Simulation Options

For instance and without limitation, simulation options may comprise one of the following or a combination thereof:
Expansion/contraction/tooth translation;
Shape of the arch;
Teeth extraction;
Interproximal reduction;
Incisal class I;
Incisal Class II (or III) compromise;
Diastema keeping;
Curve of Spee preservation; and/or
Midline position.

In one example embodiment, a virtual setup is provided based on a 3D mesh and a set of simulation options. For instance the first set of simulation options may consist in the arch type and a class I incisive. The system can then automatically align the teeth according to this first set of simulation options. Simulation options (e.g., step S116, step S190) can be adjusted based on displayed results.

Automatic Teeth Alignment

According to the selected user preferences or simulation options, the teeth represented in the initial virtual model (e.g., step S100) can be moved and realigned to the virtual setup V. In one example embodiment, the system starts by aligning the mandible teeth and then proceeds to maxillary teeth alignment with an iterative process to find the best compromise between a single arch tooth alignment (either upper or lower arch) and an occlusal arch alignment that considers both upper and lower arches.

Figure 9:
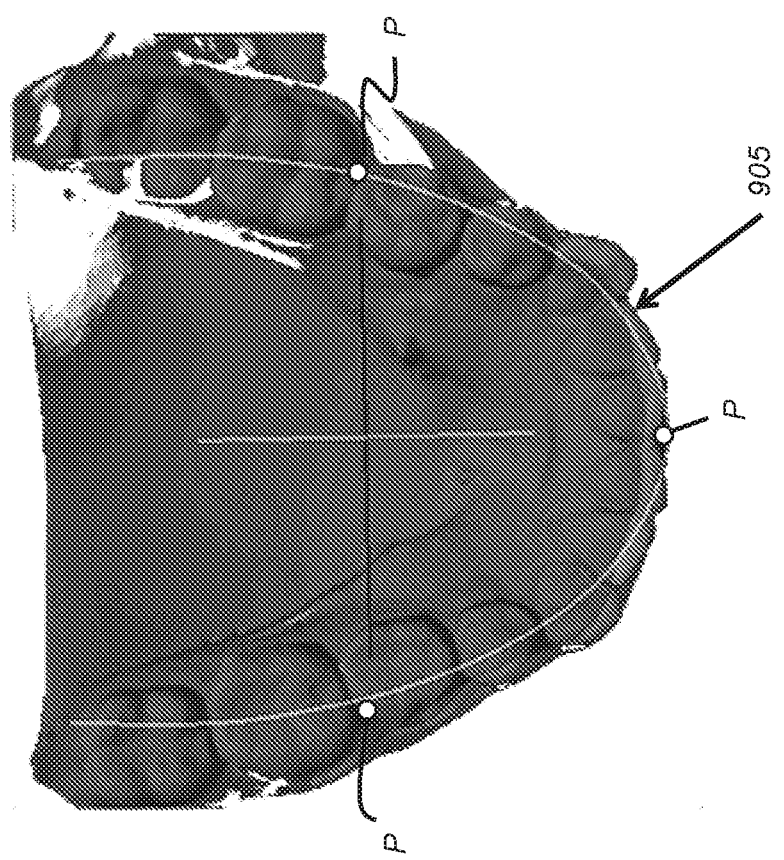
FIG. 9 shows the form of an idealized arch for simulation.

As shown in the example of FIG. 9, an ideal arch 905 can be adapted to the initial tooth arrangement virtual model, using 3 reference points P: the middle of the incisal border of the two central incisors, the mesial point of the first right molar and the mesial point of the first left molar. The ideal arch 905 can be scaled to fit these 3 points. The ideal arch 905 for the example in FIG. 9 is represented by the white curve.

In the context of the present disclosure, single arch alignment refers to an alignment of the ideal arch wherein, from the central incisors to the more distal molar, each tooth is positioned on the ideal arch using its mesial and distal points. The orientation of the tooth is adjusted to correspond to the ideal orientation (Tip and Torque). The height (Z) position of the tooth is adjusted to be in the occlusal plane of the model. In-Out values are smoothed between teeth in order to align the vestibular faces.

Adjustments for the Maxillary Arch:

The best position (Torque and Z position) of the maxillary incisors leading to a good overbite and overjet is determined automatically. The ideal arch is then updated to pass through the new central incisors position. The positions of the other teeth are updated such that they fit the updated ideal arch.

The posterior teeth are moved until they are in contact with the corresponding mandible teeth.

Determination of Metrics

Metrics are determined for evaluating the discrepancy with the desired virtual setup. The metrics can also be used in determining the set of simulation options.

Metrics threshold values may also be defined in the user preferences. The metrics threshold values can then be used to determine the set of simulation options.

For instance and without limitation, the metrics can comprise one or more of the following:
transverse canine displacement;
molar sagittal displacement;
inter-molar relationship, identifying a left-right molars position difference causing asymmetry;
incisors relationship;
posterior crossbite;
arch width expansion for molars;
molar class; incisive class, canine class; and/or
scissor bite factors, including tooth inclination angle values.

Figure 8:
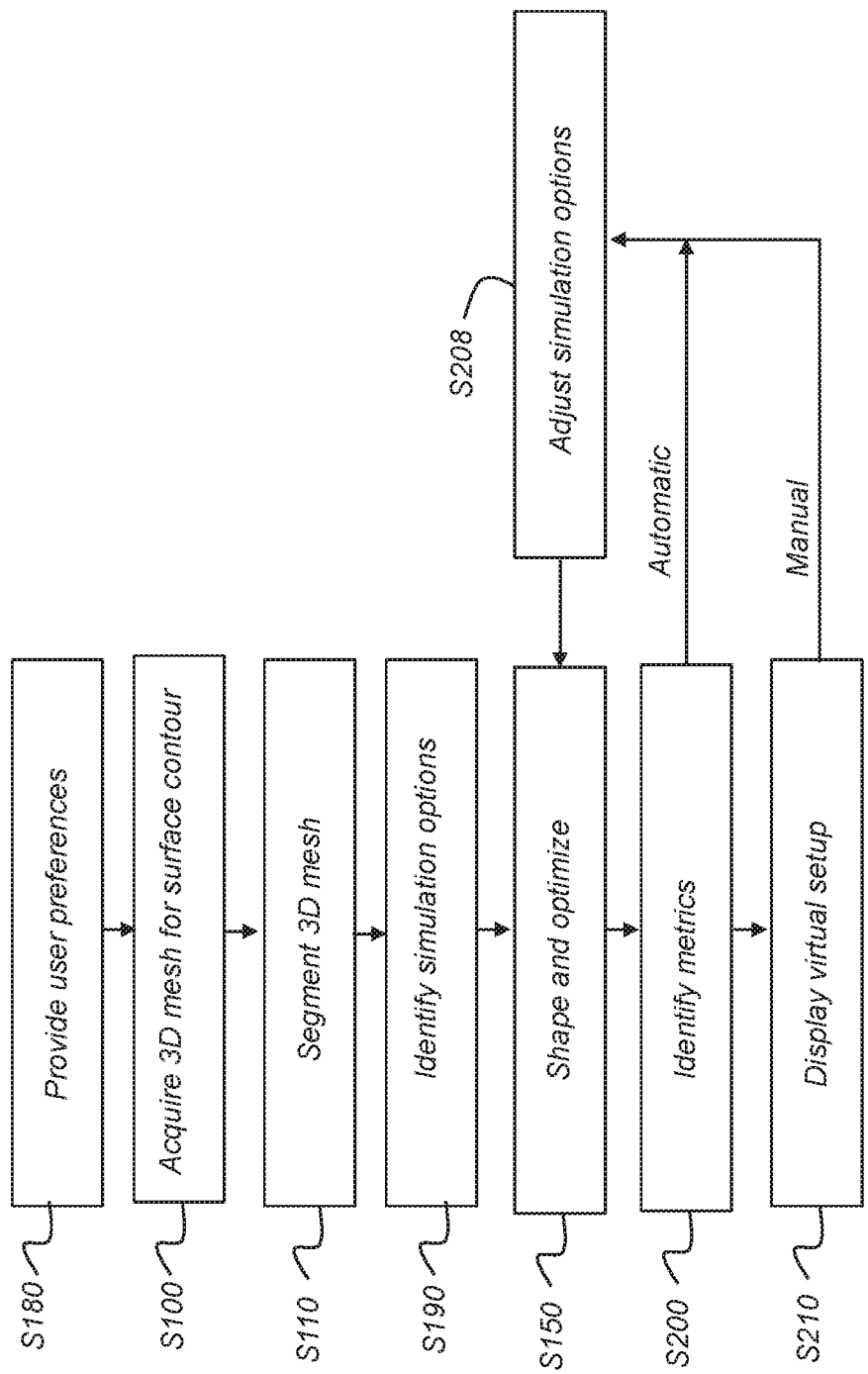
FIG. 8 is a logic flow diagram showing a sequence for segmentation and display with adjustment of simulation options.

If a particular metrics value (e.g., see step S160, step S200) does not fully satisfy the ideal standard or the user preferences, then the set of simulation options is modified and the shape and optimize step S150 (e.g., alignment) is repeated with these new simulation options, as shown in step S208 in FIG. 8. In one example embodiment, the modification of the set of simulation options (e.g., step S208) is done automatically.

Dynamic Feedback:

The automatic virtual setup V (e.g., target or final tooth arrangement) is displayed to the user on the screen. In another embodiment, the display may also show the corresponding simulation options and/or the corresponding set of metrics values.

The user can proceed to manual adjustment by changing the position of some teeth in the automatic virtual setup V. The user can also change the simulation options, which trigger another automatic tooth alignment, another virtual setup, and another metrics determination.

Figure 10A:
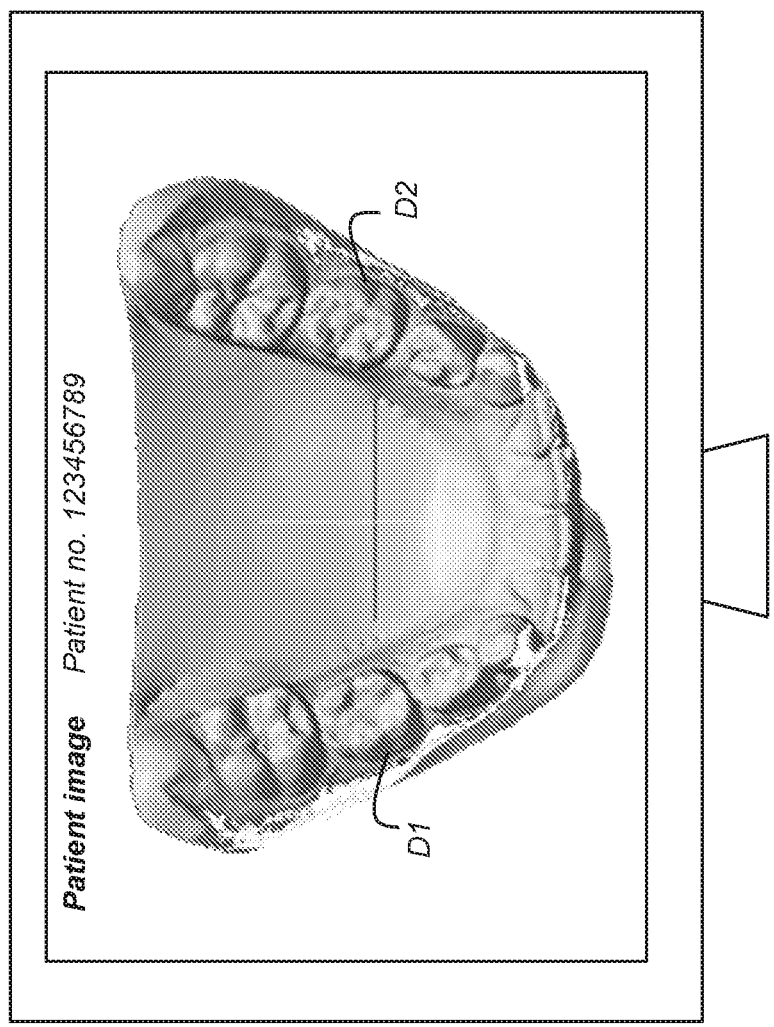
FIG. 10A shows an initial virtual tooth arrangement showing a jaw with deciduous teeth.
Figure 10B:
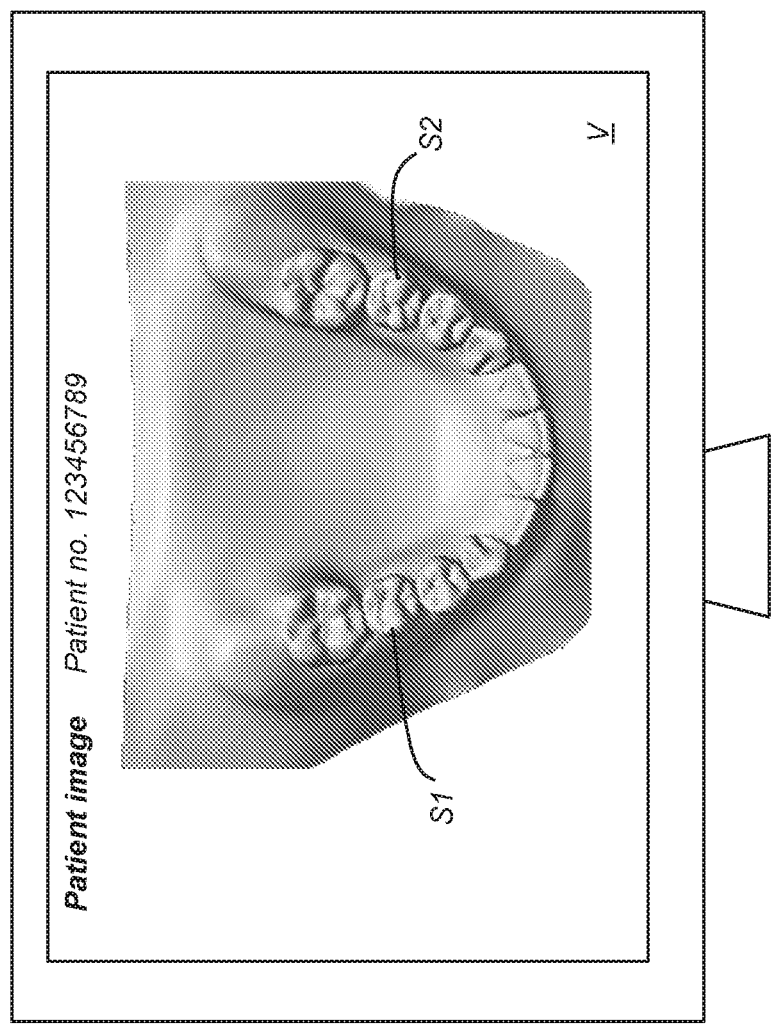
FIG. 10B shows a virtual setup with the jaw of FIG. 10A following tooth substitution.

By way of example, FIG. 10A shows a virtual model (e.g., surface contour model) of an initial tooth arrangement (e.g., step S100, step S110) for a jaw with deciduous teeth, such as D1 and D2. FIG. 10B shows a virtual setup V (for the dentition (e.g., teeth/jaw) in FIG. 10A) with jaw simulation with substitute replacement tooth models S1 and S2, respectively, according to some embodiments.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as control logic processors as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the interne or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art. Although embodiments of the present disclosure are illustrated using dental imaging apparatus, similar principles can be applied for other types of diagnostic imaging and for other anatomy. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims, and all changes that come within the meaning and range of equivalents thereof are intended to be embraced therein.

What is claimed is:

1. A method for visualizing a patient dentition orthodontic treatment comprising:
   acquiring a surface contour model of patient dentition;
   segmenting the surface contour model to identify one or more segmented teeth;
   identifying at least one unerupted tooth within the surface contour model, wherein the at least one unerupted tooth is identified using at least one of three-dimensional volume acquisition or panoramic radiography;
   accessing shape and size information for the unerupted tooth based, at least in part, on the at least one of the three-dimensional volume acquisition or the panoramic radiography;
   identifying a substitute model tooth based at least in part on the shape and size information for the unerupted tooth, wherein the substitute model tooth reflects a replacement permanent tooth model; and
   generating a virtual setup of the patient dentition, wherein a location corresponding to the at least one unerupted tooth is replaced by the replacement permanent tooth model.

2. The method of claim 1, further comprising providing a segmented cone-beam computed tomography (CBCT) 3D volume, and wherein the replacement permanent tooth model replaces an unerupted permanent tooth from the segmented CBCT 3D volume.

3. The method of claim 1, wherein the replacement permanent tooth model is an erupted permanent tooth symmetrical to the tooth.

4. The method of claim 1, wherein the replacement permanent tooth model is derived from a selected tooth model library.

5. The method of claim 1, wherein the replacement permanent tooth model is determined with a predictive model analysis using size and shape of at least one permanent tooth among the one or more segmented teeth.

6. The method of claim 1, wherein each identified segmented tooth has a corresponding mesh and a tooth margin.

7. The method of claim 1 wherein acquiring the surface contour model comprises acquiring one or more images from a CBCT apparatus, a panoramic radiography apparatus or an intraoral scanner.

8. The method of claim 1 wherein generating the virtual setup of patient dentition further comprises determining jaw size.

9. The method of claim 1 wherein one or more operator specified metrics are used for evaluating a discrepancy between a desired final tooth arrangement and the virtual setup.

10. The method of claim 1 wherein an arch shape of the generated virtual setup is modified from the arch shape of the acquired surface contour model.

11. A method for visualizing a patient dentition orthodontic treatment comprising:

receiving a plurality of segmented teeth from a virtual model of an initial tooth arrangement;

identifying at least one unerupted tooth within the surface contour model, wherein the at least one unerupted tooth is identified using at least one of three-dimensional volume acquisition or panoramic radiography;

accessing shape and size information for the unerupted tooth based, at least in part, on the at least one of the three-dimensional volume acquisition or the panoramic radiography;

identifying a substitute model tooth based at least in part on the shape and size information for the unerupted tooth, wherein the substitute model tooth reflects a replacement permanent tooth model; and generating a virtual setup of a target tooth arrangement wherein a location corresponding to the at least one tooth is replaced by the replacement permanent tooth model.

12. The method of claim 11, further comprising providing a segmented CBCT 3D volume or segmented panoramic radiography image, and wherein the corresponding permanent tooth model replaces an unerupted permanent tooth from the segmented CBCT 3D volume or segmented panoramic radiography image.

13. The method of claim 11, wherein the corresponding permanent tooth model is determined based on an erupted permanent tooth symmetrical to the unerupted tooth, derived from a selected tooth model library, or determined with a predictive model analysis using size and shape of at least one permanent tooth among the one or more segmented teeth.

14. The method of claim 11, wherein the receiving a plurality of segmented teeth further comprises:

acquiring a 3D mesh of the initial tooth arrangement; and segmenting the 3D mesh to identify the plurality of segmented teeth, wherein each segmented tooth has a corresponding mesh and a tooth margin.

15. The method of claim 11, further comprising:

accepting operator selections of one or more preferences and corresponding metrics that relate to changes in the initial tooth arrangement, where the virtual setup simulates patient dentition according to the operator selected preferences and the corresponding metrics.

16. The method of claim 15 further comprising displaying at least one of the operator selected preferences and corresponding metrics with the virtual setup.

17. The method of claim 16, further comprising:

accepting a subsequent operator selection to modify at least one selected preference and corresponding metric;

re-generating the virtual setup that simulates the patient dentition according to the at least one subsequent operator modified preference and corresponding metric; and displaying the at least one subsequent operator modified preference and corresponding metric with the re-generated virtual setup.

18. The method of claim 15 wherein the one or more preferences relate to maxillary arch type, mandibular arch type, inter-canine width expansion, flattening parameters for shaping the arch curve, tooth translation, arch expansion and tooth translation, arch contraction and tooth translation, tooth extraction, tooth extraction order, interproximal reduction, and occlusal class treatment type.

19. The method of claim 11 further comprising accepting operator selections of one or more simulation options, wherein the simulation options relate to one or more of arch expansion and tooth translation, arch contraction and tooth translation, or interproximal reduction and tooth translation.

20. An apparatus for providing a virtual setup for orthodontics assessment, the apparatus comprising:

an imaging apparatus configured to acquire a surface contour of patient dentition;

a processor programmed with instructions that
  (i) segment the dentition surface contour to identify one or more segmented teeth;
  (ii) identify at least one unerupted tooth within the surface contour model, wherein the at least one unerupted tooth is identified using at least one of three-dimensional volume acquisition or panoramic radiography;
  (iii) access shape and size information for the unerupted tooth based, at least in part, on the at least one of the three-dimensional volume acquisition or the panoramic radiography;
  (iv) identify a substitute model tooth based at least in part on the shape and size information for the unerupted tooth, wherein the substitute model tooth reflects a replacement permanent tooth model;
  (v) generate a virtual setup of a target dentition arrangement, wherein a location corresponding to the at least one unerupted tooth is replaced by the corresponding permanent tooth model; and a display in signal communication with the processor, and configured to display the virtual setup.

* * * * *